US00PP31361P2

(12) United States Plant Patent
Villegas

(10) Patent No.: US PP31,361 P2
(45) Date of Patent: Jan. 14, 2020

(54) ***SANSEVIERIA* PLANT NAMED 'YELLOWSTONE'**

(50) Latin Name: *Sansevieria aubrytiana*
Varietal Denomination: YELLOWSTONE

(71) Applicant: FLORICA FARMS, INC., Eustis, FL (US)

(72) Inventor: Marvin Gonzalez Villegas, Alajuela (CR)

(73) Assignee: FLORICA FARMS, INC., Eustis, FL (US)

( * ) Notice: Subject to any disclaimer, the term of this patent is extended or adjusted under 35 U.S.C. 154(b) by 0 days.

(21) Appl. No.: 16/350,821

(22) Filed: Jan. 17, 2019

(51) Int. Cl.
*A01H 5/02* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 5/02
See application file for complete search history.

*Primary Examiner* — Kent L Bell
(74) *Attorney, Agent, or Firm* — Foley & Lardner LLP

(57) ABSTRACT

A new and distinct cultivar of *Sansevieria aubreytiana* plant named 'YELLOWSTONE', particularly characterized by its variegated foliage with irregular, differently green toned bands with light green toned margin bands; wide and lanceolate leaves, supported in a rosette; 50-80 cm plant height; erect plant habit; and high drought tolerance with low need for water.

3 Drawing Sheets

Figure 1:
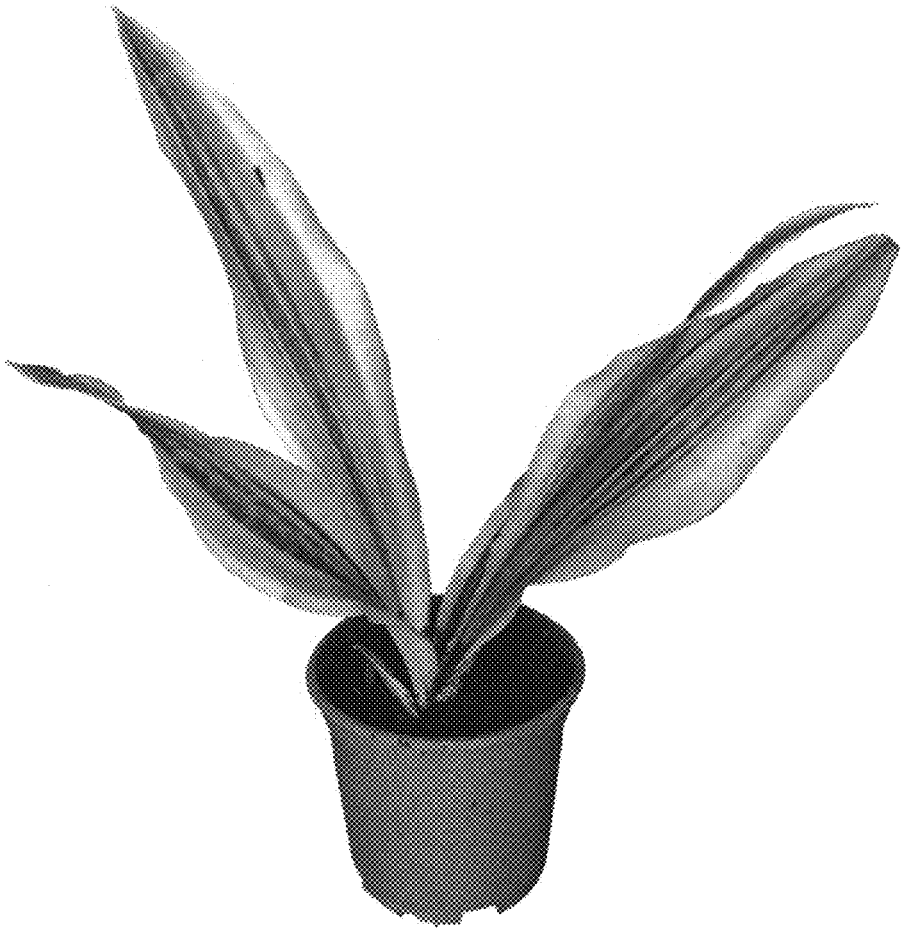

Latin name of the genus and species of the claimed plant: *Sansevieria aubrytiana.*

Variety denomination: 'Yellowstone'.

BACKGROUND OF THE INVENTION

The present invention relates to a new and distinct cultivar of *Sansevieria* plant, botanically known as *Sansevieria aubrytiana*, of the family Ruscaceae, hereinafter referred to by the cultivar name 'YELLOWSTONE'.

*Sansevieria* is a monocotyledonous and succulent plant, which can be produced in either hard-leafed or soft-leafed varieties for interior use as a house plant or outdoors ornamental plant.

The new variety 'YELLOWSTONE' originated as a naturally-occurring mutation of the *Sansevieria aubrytiana* variety 'SAYURI' (unpatented). The new *Sanseviera* 'YELLOWSTONE' was discovered and selected by the inventor Marvin Gonzalez Villegas, as a single sprouting rare mutated plant in a controlled environment, on a plantation growing *Sansevieria aubrytiana* 'SAYURI', in 2016 in Monterrey, San Carlos, Alajuela province, Costa Rica.

Asexual reproduction of the new *Sansevieria* cultivar by vegetative cuttings was first performed in 2016 in Monterrey, San Carlos, Alajuela, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'YELLOWSTONE', which in combination distinguish this *Sansevieria* as a new and distinct cultivar:

1. Variegated foliage with different green tones on the irregular bands, and light green colored margin bands in the leaf blade
2. Wide and lanceolate leaves, supported in a rosette.
3. 50-80 cm plant height.
4. Erect plant habit.
5. Needs little water and is very drought tolerant.

The new variety 'YELLOWSTONE' is considered a variety of *Sansevieria* in the group denominated as "long leaves *Sansevieria* varieties". The new variety presents an average of 4-6 leaves per plant when it reaches its maturity (between 6-10 months). The new variety has an erect growth habit and the entire plant can reach a height range between 50-80 cm. The leaves are slightly wide (7-10 cm average measured at the widest part of the mature leaf) and lanceolate, with a soft waxy texture. The blades are thin and slightly wavy. The plant has a cylindrical shape.

The new variety is moderately drought tolerant, adapts to conditions of light and shade (interior and exterior), and shows resistance to antrachnose (*Colletotrichum sansvierae*) disease.

The leaf blade is yellow colored (RHS 4C), with non-uniform dark green vertical variegated bands on both sides of the leaves (RHS 141A, and 141C.)

The variety 'SAYURI' gave rise to the variety 'YELLOWSTONE'. The 'SAYURI' is also considered part of the "long leaves varieties" group. The claimed variety shows a lower number of leaves per plant (4-6) than 'SAYURI', and more wide with an average width of 7-10 cm (measured in the middle of the mature leaf.) The growth habit is erect and presents narrow leaves supported in a rosette. The entire plant can reach a size between 50-80 cm. The plant has, as for 'SAYURI', a cylindrical shape.

Plants of the new *Sansevieria* 'YELLOWSTONE' differ from plants of the parental cultivar, 'SAYURI' (unpatented) in the characteristics described in Table 1.

TABLE 1

Comparison between new cultivar 'YELLOWSTONE' and its parent variety 'SAYURI'.

| Characteristic | New Cultivar 'YELLOWSTONE' | Parent 'SAYURI' (unpatented) |
|---|---|---|
| Plant Vigor | less vigorous (less leaves) | more vigorous (more leaves) |
| Color | variegated leaves (different green tones and, brighter andcontrasting yellow tones on the irregular bands) | variegated leaves (different green and white tones on the irregular bands) |
| Shape | wide and lanceolated leaves on a rosette | wide and lanceolated leaves on a rosette |
| Texture of leaves | smooth-textured leaves | smooth-textured leaves |

Of the many commercial cultivars known to the present inventor, the most similar in comparison to the new *Sansevieria* 'YELLOWSTONE' is the *Sansevieria* 'SAYURI'.

BRIEF DESCRIPTION OF THE PHOTOGRAPHS

The accompanying photographs illustrate the overall appearance of the new *Sansevieria* cultivar 'YELLOWSTONE' showing the colors as true as is reasonably possible with colored reproductions of this type. Colors in the photographs may differ slightly from the color value cited in the detailed botanical description which accurately describe the color of 'YELLOWSTONE'.

FIG. 1—Shows a side view of a six-month old plant of *Sansevieria* 'YELLOWSTONE' in a 26 cm diameter pot.

Figure 2:
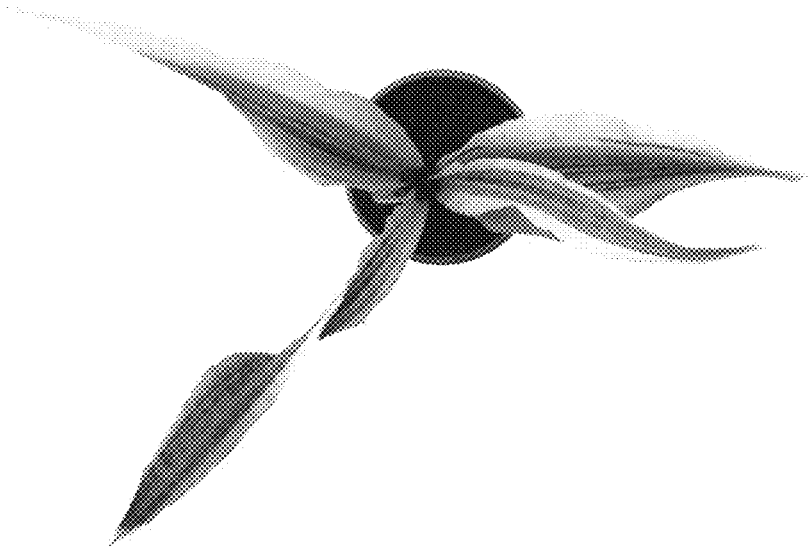

FIG. 2—Shows a top down view of a typical six-month-old plant of *Sansevieiria* 'YELLOWSTONE'.

Figure 3:
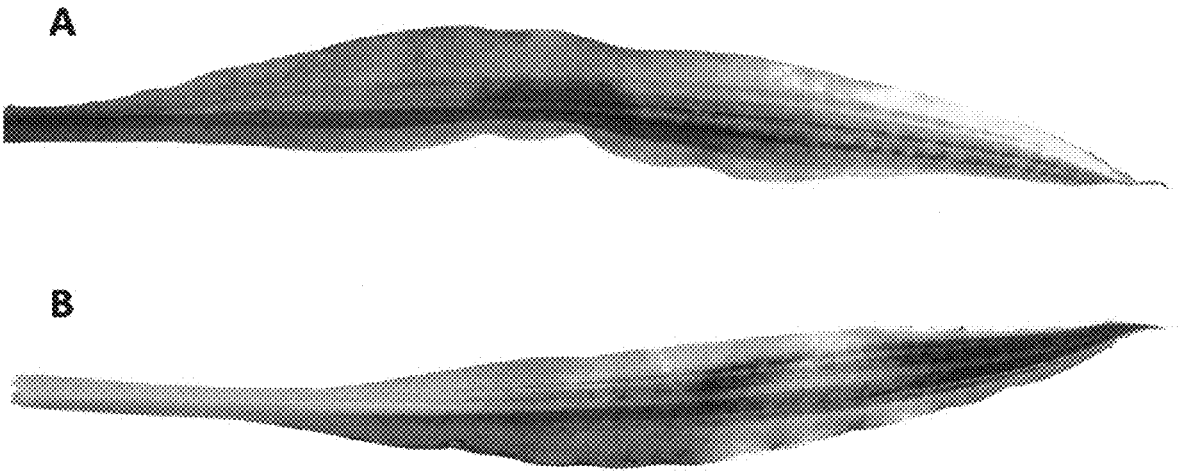

FIG. 3—shows a close-up view of the typical leaves of *Sansevieria* 'YELLOWSTONE' from a six-month old plant (upper side—A, under side—B).

DETAILED BOTANICAL DESCRIPTION

The new *Sansevieria* 'YELLOWSTONE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'YELLOWSTONE' as grown in open-field conditions at Monterrey, San Carlos, Alajuela province, Costa Rica, under conditions which closely approximate those generally used in commercial practice. 24.5° C. during the day and 18° C. at night. Plants grow under natural light conditions.

This crop does not require constant fertilization, to increase production per area about 200 kg ha−1 N, 150 kg ha−1 of P and 100 kg ha−1 K are required, the production is closely related with soil conditions in which they are grown.

Color references are made to The Royal Horticultural Society Colour Chart, except where general colors of ordinary significance are used. The photographs and descriptions were taken during the rainy season in Monterrey, San Carlos, Alajuela province, Costa Rica when outdoor day temperature was 23° C. The age of the plants described is 6 months.

Classification:

*Botanical.*—*Sansevieria aubrytiana.*

*Variety denomination: 'YELLOWSTONE'.*

Parentage: *Sansevieria aubrytiana* 'SAYURI' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to temperatures between 12° C. and 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit description.*—Rhizomes, with short roots.

*Time to initiate roots.*—15 to 22 days at 20-25° C.

*Faster time to produce a rooted cutting.*—About 60 to 90 days at 20-25° C.

Plant:

*General appearance and form.*—

*Height.*—About 80 cm when grown in ground; about 50 cm when grown in a 26 cm size container.

*Spread.*—About 15 cm when grown in ground; About 12 cm when grown in 26 cm size container.

*Form.*—Monocot; leaf bases arranged in a rosette around growth point.

*Shape.*—Cylindrical.

*Growth rate and habit.*—About 2 cm per week; upright.

*Fragrance.*—None.

*Stem.*—Modified (Rhizome and foliage). Length: About 12 cm when grown in ground; About 8 cm when grown in 21 cm size container. Diameter: About 3.0-4.0 cm. Shape: round. Texture: rough. Color: RHS 4D. Strength: strong and durable. Inter node length: About 0.6 mm to 0.8 mm.

Foliage:

*Quantity.*—About 4-6 leaves.

*Arrangement and attachment.*—Single, alternate; leaf bases arranged in a rosette around growth point.

*Leaf length.*—About 30 cm.

*Leaf width.*—About 9 cm.

*Overall shape of leaf: Lanceolated.*

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS 4C, RHS141A and RHS141C. Lower Surface: RHS 4C, RHS141A and RHS141C.

*Color of immature leaf.*—Upper Surface: RHS 4C, RHS141A and RHS141C. Lower Surface: RHS 4C, RHS141A and RHS141C.

*Venation.*—Pattern: longitudinal/parallel leaf shape. Color: None. Leaf fragrance: None.

Inflorescence description:

*Arrangement and type.*—Inflorescence.

*Orientation at opening.*—Out of the spike.

*Quantity, per plant with at least one open flower.*—About 60 at 2 weeks.

*Inflorescence size*.—Length: About 35 cm. Diameter: About 1.2 cm.

*Flower size*.—Length: About 6 cm. Diameter: About 0.5 cm. Depth: About 1 cm.

*Fragrance*.—None.

*Rate of opening*.—About 7 to 8 days, according to weather.

*Shape*.—Ovoid.

*Length*.—About 2 cm.

*Diameter*.—About 1 cm.

*Color*.—Apex: RHS 149 B. Base: RHS 142 B.

*Texture* (*both surfaces*).—Smooth.

Reproductive organs:

*Androecium*.—Stamen: Number: 6 per flower. Length: About 1.2 mm. Color: RHS 150D. Anther: Length: About 4 mm. Width: About 1 mm. Color: RHS 150D. Filament: Length: About 1.3 mm. Color: RHS 150 D. Pollen: Amount: moderate. Color: RHS 150D.

*Gynoecium*.—Pistil: Number: One per flower. Length: About 1.5 mm. Stigma: Length: About 0.5 mm. Width: About 1 mm. Color: RHS 150D. Style: Length: About 20 mm. Color: RHS 150D. Ovary: Length: About 5 mm. Width: About 4 mm. Color: RHS 143A.

What is claimed is:

1. A new and distinct variety of *Sansevieria aubreytiana* plant named 'YELLOWSTONE', substantially as illustrated and described herein.

* * * * *